US007002028B2

(12) United States Patent
White et al.

(10) Patent No.: US 7,002,028 B2
(45) Date of Patent: Feb. 21, 2006

(54) 5-ANDROSTEN-3β-OL STEROID INTERMEDIATES AND PROCESSES FOR THEIR PREPARATION

(75) Inventors: Michael J. White, Portage, MI (US); Peter Guillaume Marie Wuts, Mattawan, MI (US); Doris Beck, Kalamazoo, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/858,177

(22) Filed: Jun. 1, 2004

(65) Prior Publication Data

US 2004/0220158 A1 Nov. 4, 2004

Related U.S. Application Data

(62) Division of application No. 10/392,955, filed on Mar. 21, 2003.

(60) Provisional application No. 60/415,293, filed on Oct. 1, 2002, provisional application No. 60/403,990, filed on Aug. 16, 2002.

(51) Int. Cl.
C07J 1/00 (2006.01)
(52) U.S. Cl. ...................... 552/615; 552/612
(58) Field of Classification Search ................. 552/612, 552/615
See application file for complete search history.

(56) References Cited

U.S. PATENT DOCUMENTS

| | | | |
|---|---|---|---|
| 3,294,646 A | 12/1966 | Smith et al. ................. 195/51 |
| 4,031,074 A | 6/1977 | deJongh et al. ........ 260/239.55 |
| 4,045,574 A | 8/1977 | Kerb et al. ................. 424/303 |
| 4,054,563 A | 10/1977 | Anner et al. ........... 260/239.55 |
| 4,056,633 A | 11/1977 | Kerb et al. ................. 424/331 |
| 4,196,203 A | 4/1980 | Kapp et al. ................. 424/242 |
| 4,336,332 A | 6/1982 | Fujiwara et al. ............. 435/58 |
| 4,416,985 A | 11/1983 | Petzoldt et al. .............. 435/58 |
| 4,559,332 A | 12/1985 | Grob ......................... 514/175 |
| 4,614,616 A | 9/1986 | Petzoldt et al. ............... 540/4 |
| 5,981,744 A | 11/1999 | Ng et al. ..................... 540/41 |
| 6,046,023 A | 4/2000 | Wiersma et al. .............. 435/60 |

FOREIGN PATENT DOCUMENTS

FR 2771105 11/1997

OTHER PUBLICATIONS

Bell, AM et al 'Microbiological hydroxylation. XX. Hydroxylation of dioxygenated 5 alpha-androstanes with the fungi *Absidia regnieri* and *Syncephelastrum racemosum*' CA 84:5238 (1976).*
Wuts, PGM et al 'New process for the preparation of methyl caronates' Organic Letters vol. 5(9) p. 1483-1485 (2003).*
Adams, JB et al 'Preparation and reactions of 7αhydroxy and 7βhydroxydehydroepiandroseterone' CA 77:62217 (1972).*
Bensasson, C.M., et al., "The Hydroxylation of β-Androstenes by *Cephalosporium Aphidicola*", Phytochemistry, vol. 49, (8), pp. 2355-2358 (1998).
Cotillon, A-C., et al., "*The Inducible and Cytochrome P450-Containing Dehydroepiandrosterone 7 α-Hydroxylating Enzyme System of Fusarium moniliforme*", J. Steroid Biochem. Molec. Biol., vol. 62 (5/6), pp. 467-475 (1997).
Cotillon, A-C. & R. Morfin, "*Transformation of 3-hydroxy-steroids by Fusarium moniliforme 7 α-hydroxyllase*", J. Steroid Biochem. Molec. Biol., vol. 68, pp. 229-237 (1999).
Kolek, Teresa, "*Biotransformation XLVII: transformations of 5-ene steroids in Fusarium culmorum culture*", J. Steroid Biochem. Molec. Biol., vol. 71, pp. 83-90 (1999).
Madyastha, K.M. & T. Joseph, "*Transformation of dehydroepiandrosterone and pregnenolone by Mucor piriformis*", Appl. Microbiol. Biotechiol, vol. 44, pp. 339-343 (1995).
Wilson, M.R., et al., "*Steroid transformations with Fusarium oxysporum var. cubense and Collectotrichum musae*", Steroids, vol. 64, pp. 834-843 (1999).
Wuts, P.G.M., and A.R. Ritter, "A Novel Synthesis of Spironolactone. An Application of the Hydroformylation Reaction", J. Org. Chem., vol. 54, pp. 5180-5182 (1989).

* cited by examiner

*Primary Examiner*—Amelia A. Owens
(74) *Attorney, Agent, or Firm*—Steven R. Eck; Charles W. Ashbrook

(57) ABSTRACT

The present invention provides 5-androsten-3β-ol steroid intermediates and processes for their preparation.

2 Claims, No Drawings

5-ANDROSTEN-3β-OL STEROID INTERMEDIATES AND PROCESSES FOR THEIR PREPARATION

CROSS-REFERENCE TO RELATED APPLICATIONS

This application is a division of U.S. application Ser. No. 10/392,955 filed on Mar. 21, 2003, which is now pending. Which also claims benefit of U.S. Application Ser. No. 60/415,293 filed on Oct. 1, 2002.

FIELD OF THE INVENTION

The present invention provides 5-androsten-3β-ol steroids and processes for their preparation.

BACKGROUND

Steroid intermediates are often useful in the production of pharmaceutical agents. 5-androsten-3β,7β,11α-triol-17-one is a steroid intermediate useful for producing eplerenone.

SUMMARY OF INVENTION

In general, the present invention provides a practical fungal method for 7β- and 11α-hydroxylation of 5-androsten-3β-ol-17-one and other related analogues of the general formula (I) to yield 5-androsten-3β,7β,11α-triol-17-one and other related analogues of the general formula (II and IV).

In one aspect, the invention features a 7β-hydroxy steroid of the formula (II)

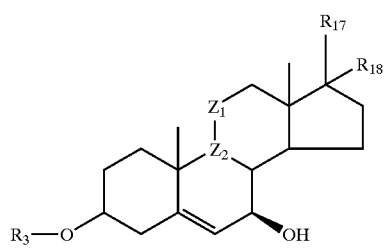

where $R_3$ is:
(1) —H;
(2) —CO—$R_4$
where $R_4$ is H or $C_1$–$C_5$ alkyl;
where $R_{17}$ and $R_{18}$ together form =O or
where $R_{17}$ and $R_{18}$ together with the C17 carbon atom of the steroid backbone to which they are bound form a lactone ring of the formula

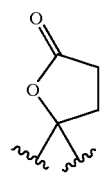

where $Z_1$–$Z_2$ is either a single bond, or a double bond. Examples of the 7β-hydroxy steroid (II) include, but are not limited to, 5-androsten-3β,7β-diol-17-one and 5,9(11)-androstadien-3β,7β-diol-17-one.

In another aspect, the invention features a 11α-hydroxy steroid of the formula (III)

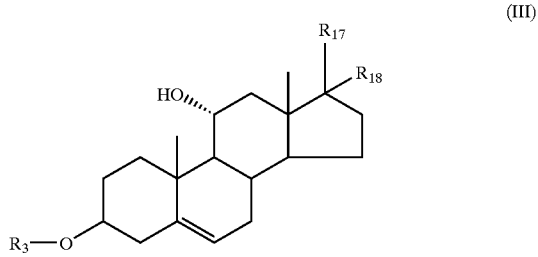

where $R_3$ is:
(1) —H;
(2) —CO—$R_4$
where $R_4$ is H or $C_1$–$C_5$ alkyl;
where $R_{17}$ and $R_{18}$ together form =O or
where $R_{17}$ and $R_{18}$ together with the C17 carbon atom of the steroid backbone to which they are bound form a lactone ring of the formula

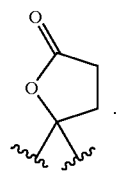

An example of the 11α-hydroxy steroid of formula (III) is 5-androsten-3β,11α-diol-17-one.

In another aspect, the invention features a 7β,11α-dihydroxy steroid of the formula (IV)

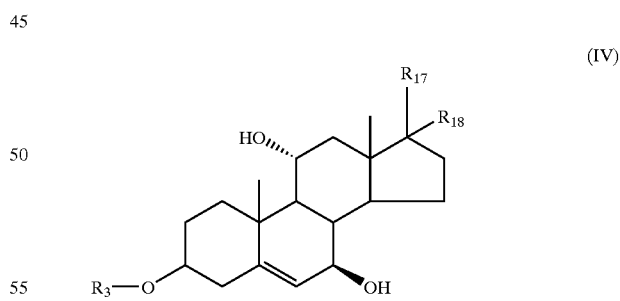

where $R_3$ is:
(1) —H;
(2) —CO—$R_4$
where $R_4$ is H or $C_1$–$C_5$ alkyl;
where $R_{17}$ and $R_{18}$ together form =O or
where $R_{17}$ and $R_{18}$ together with the C17 carbon atom of the steroid backbone to which they are bound form a lactone ring of the formula

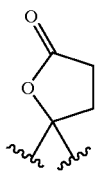

An example of the 7β,11α-dihydroxy steroid of formula (IV) is 5-androsten-3β,7β,11α-triol-17-one.

In still another aspect, the invention features a process for the preparation of a 7β-hydroxy steroid of the formula (II)

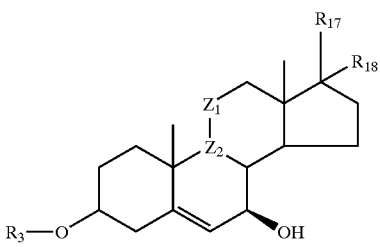

(II)

where $R_3$ is:
(1) —H;
(2) —CO—$R_4$
where $R_4$ is H or $C_1$–$C_5$ alkyl;
where $R_{17}$ and $R_{18}$ together form =O or
where $R_{17}$ and $R_{18}$ together with the C17 carbon atom of the steroid backbone to which they are bound form a lactone ring of the formula

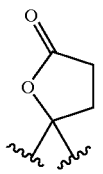

where $Z_1$–$Z_2$ is either a single bond, or a double bond, the process comprising
(1) contacting a Δ⁵-steroid of formula (I)

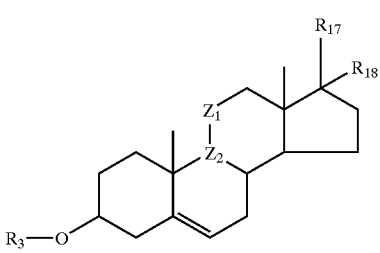

(I)

where $R_3$, $R_{17}$, $R_{18}$, and $Z_1$–$Z_2$ are as defined above, with 7β-hydroxylase of *Diplodia*, e.g., *Diplodia gossypina*. Examples of the 7β-hydroxy steroid (II) include, but are not limited to, 5-androsten-3β,7β-diol-17-one and 5,9(11)-androstadien-3β,7βp-diol-17-one. The process of contacting may be by fermentation, cell concentrate, whole cells or cell-free reaction.

In another aspect, the invention features a process for the preparation of an 11α-hydroxy steroid of the formula (III)

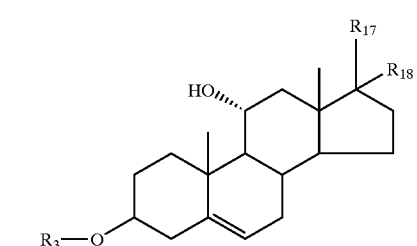

(III)

where $R_3$ is:
(1) —H;
(2) —CO—$R_4$
where $R_4$ is H or $C_1$–$C_5$ alkyl;
where $R_{17}$ and $R_{18}$ together form =O or
where $R_{17}$ and $R_{18}$ together with the C17 carbon atom of the steroid backbone to which they are bound form a lactone ring of the formula

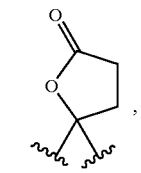

the process comprising:
(1) contacting a Δ⁵-steroid of formula (I)

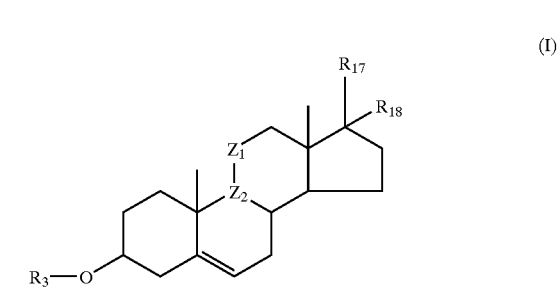

(I)

where $R_3$, $R_{17}$, and $R_{18}$ are as defined above and where $Z_1$–$Z_2$ is a single bond with 11α-hydroxylase of *Aspergillus*, e.g., *Aspergillus ochraceus*. An example of the 11α-hydroxy steroid is 5-androsten-3β,11α-diol-17-one. The process of contacting may be by fermentation, cell concentrate, whole cells or cell-free reaction.

In yet another aspect, the invention features a process for the preparation of a 7β,11α-dihydroxy steroid of the formula (IV)

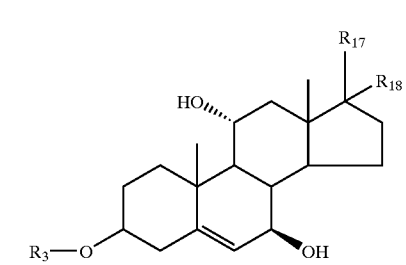

(IV)

where $R_3$ is:
(1) —H;
(2) —CO—$R_4$
where $R_4$ is H or $C_1$–$C_5$ alkyl;
where $R_{17}$ and $R_{18}$ together form =O or

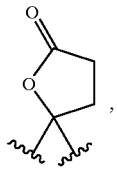

the process comprising
(1) contacting a $\Delta^5$-steroid of formula (I)

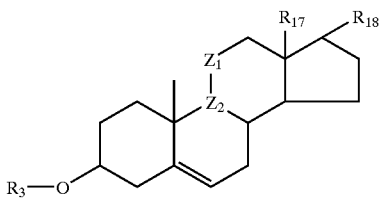

where $R_3$, $R_{18}$, and $R_{17}$ are as defined above and where $Z_1$–$Z_2$ is a single bond between with 7β-hydroxylase of *Diplodia*, e.g., *Diplodia gossypina*, to produce a 7β-hydroxy steroid of formula (II)

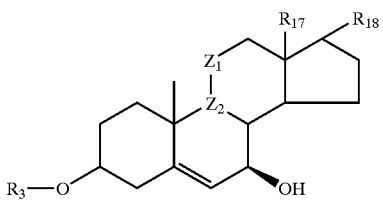

where $R_3$, $R_{17}$, $R_{18}$, and $Z_1$–$Z_2$ are as defined above; and
(2) contacting the 7β-hydroxy steroid (II) of step (1) with 11α-hydroxylase of *Aspergillus*, e.g., *Aspergillus ochraceus*. An example of the 7β,11α-dihydroxy steroid (IV) is 5-androsten-3β,7β,11α-triol-17-one. The process for the preparation of a 7β,11α-dihydroxy steroid (IV) where the 7β-hydroxy steroid (II) of step (1) may not be isolated prior to the contacting of step (2).

In another aspect, the invention features a process for the preparation of a 7β,11α-dihydroxy steroid of the formula (IV)

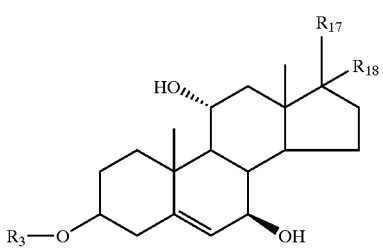

where $R_{17}$ and $R_{18}$ together with the C17 carbon atom of the steroid backbone to which they are bound form a lactone ring of the formula

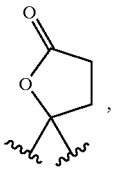

the process comprising
(1) contacting a 7β-hydroxy steroid of formula (II)

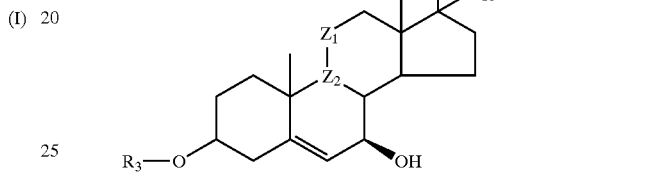

where $R_3$, $R_{17}$, and $R_{18}$ are as defined above and where $Z_1$–$Z_2$ is a single bond with 11α-hydroxylase of *Aspergillus*, e.g., *Aspergillus ochraceus*. An example of the 7β,11α-dihydroxy steroid (IV) is 5-androsten-3β,7β,11α-triol-17-one. The process of contacting may be by fermentation, cell concentrate, whole cells or cell-free reaction.

In still a further aspect, the invention features a process for the preparation of a 7β,11α-dihydroxy steroid of the formula (IV)

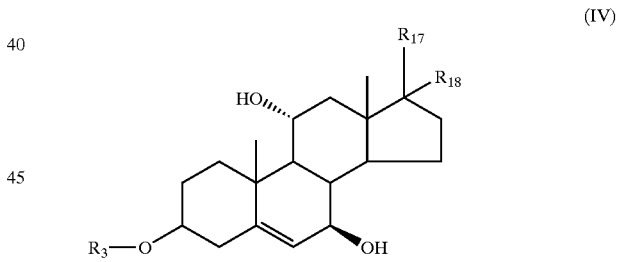

where $R_3$ is:
(1) —H;
(2) —CO—$R_4$
where $R_4$ is H or $C_1$–$C_5$ alkyl;
where $R_{17}$ and $R_{18}$ together form =O or
where $R_{17}$ and $R_{18}$ together with the C17 carbon atom of the steroid backbone to which they are bound form a lactone ring of the formula where $R_3$ is:
(1) —H;
(2) —CO—$R_4$
where $R_4$ is H or $C_1$–$C_5$ alkyl;
where $R_{17}$ and $R_{18}$ together form =O or
where $R_{17}$ and $R_{18}$ together with the C17 carbon atom of the steroid backbone to which they are bound form a lactone ring of the formula

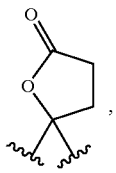, the process comprising
(1) contacting a $\Delta^5$-steroid of formula (I)

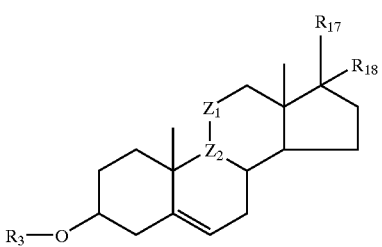

where $R_3$, $R_{18}$, and $R_{17}$ are as defined above and where $Z_1$-$Z_2$ is a single bond with the 7β,11α-hydroxylase(s) of *Absidia*, e.g., *Absidia coerulea*. An example of the 7β,11α-dihydroxy steroid (IV) is 5-androsten-3β,7β,11α-triol-17-one. The process of contacting may be by fermentation, cell concentrate, whole cells or cell-free reaction.

In yet another aspect, the invention features process for the preparation of a 5,9(11)-androstadien of formula I

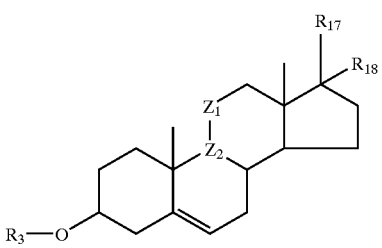

where $R_3$ is:
(1) —H;
(2) —CO—$R_4$
where $R_4$ is H or $C_1$-$C_5$ alkyl;
where $R_{17}$ and $R_{18}$ together form =O or
where $R_{17}$ and $R_{18}$ together with the C17 carbon atom of the steroid backbone to which they are bound form a lactone ring of the formula

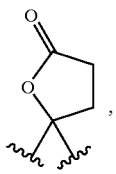, and where $Z_1$-$Z_2$ is a double bond, the process comprising:
(1) providing a compound of the formula (III)

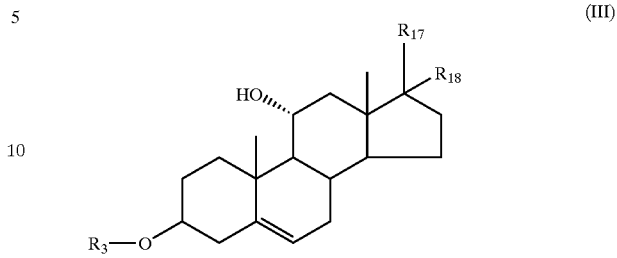

where $R_3$, $R_{17}$, and $R_{18}$ are as defined above; and (2) eliminating the 11α hydroxyl group to form the double bond between $Z_1$ and $Z_2$ (Formula I). The step of providing the compound of formula III may include contacting a $\Delta^5$-steroid of formula (I)

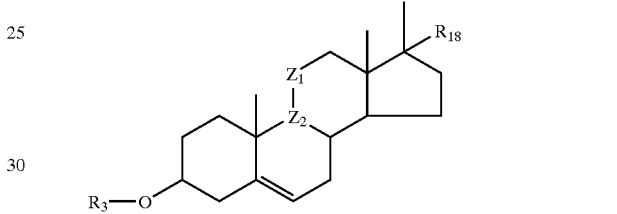

where $R_3$, $R_{17}$, and $R_{18}$ are as defined above and where $Z_1$-$Z_2$ is a single bond with 11α-hydroxylase of *Aspergillus*, e.g., *Aspergillus ochraceus*.

Embodiments of each aspect of the invention may include one or more of the following. $R_3$ is H. $R_3$ is —C(O)—CH$_3$. $R_3$ is —C(O)—H. $R_{17}$ and $R_{18}$ form =O. $R_{17}$, $R_{18}$, and the C17 carbon atom of the steroid backbone form the lactone ring shown above. The lactone ring has the α and β stereochemistry shown in the formula

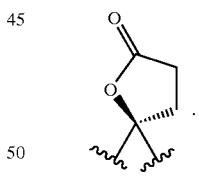

DEFINITIONS AND CONVENTIONS

The definitions and explanations below are for the terms as used throughout this entire document including both the specification and the claims.

Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_i$" or "$R_i$" where "i" is an integer.

Definitions

The definitions and explanations below are for the terms as used throughout this entire document including both the specification and the claims.

All temperatures are in degrees Celsius.
r.p.m. refers to revolutions per minute.
TLC refers to thin-layer chromatography.
HPLC refers to high pressure liquid chromatography.
psig refers to pounds per square inch gage.
DO refers to dissolved oxygen.
RO refers to reverse osmosis.
SLM refers to standard liters per minute.
VVM refers to volume per minute.
OUR refers to oxygen uptake rate.
When solvent mixtures are used, the ratios of solvents used are volume/volume (v/v).

DETAILED DESCRIPTION OF THE INVENTION

In general the invention relates to 7β,11α-dihydroxysteroids and processes for their preparation. Compounds of this invention may be used in the production of Eplerenone. Scheme I illustrates one possible method for using a 7β,11α-dihydroxysteroids to produce Eplerenone.

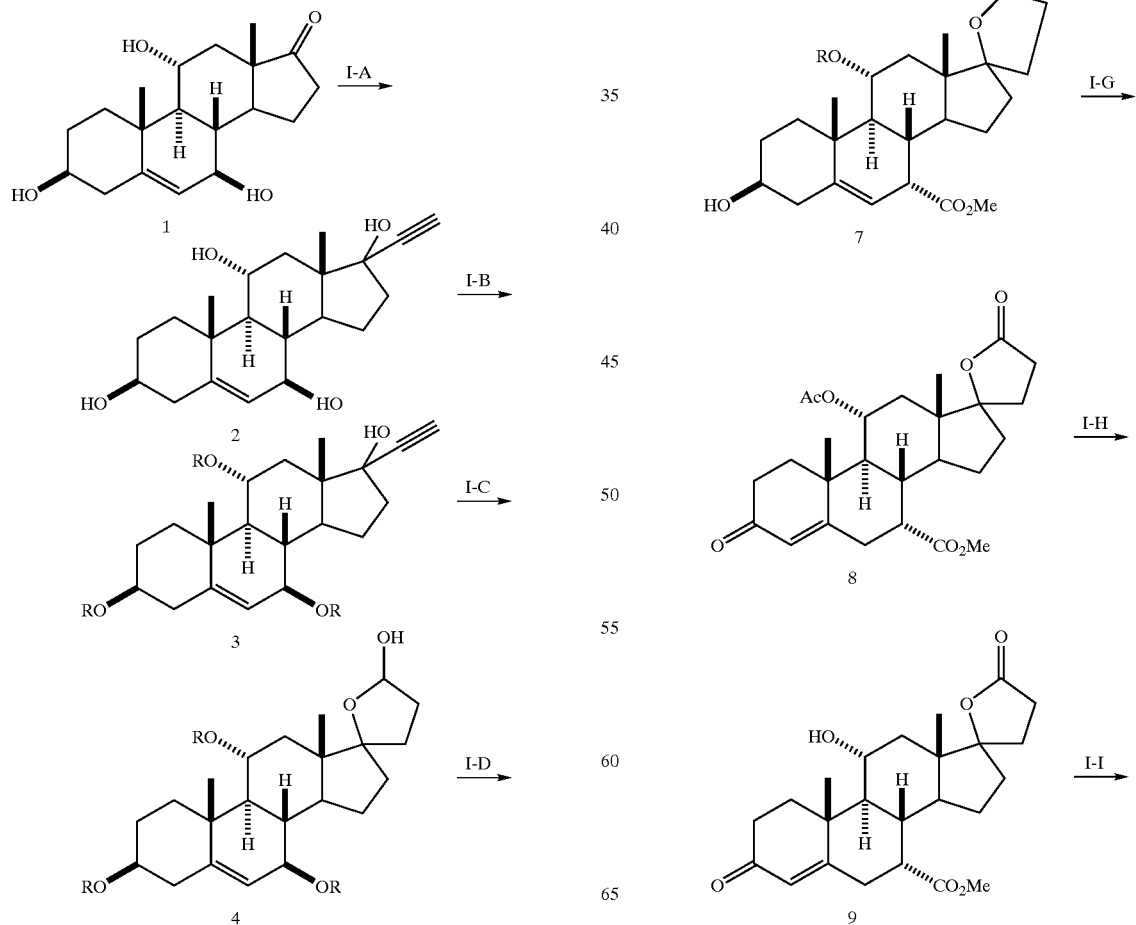

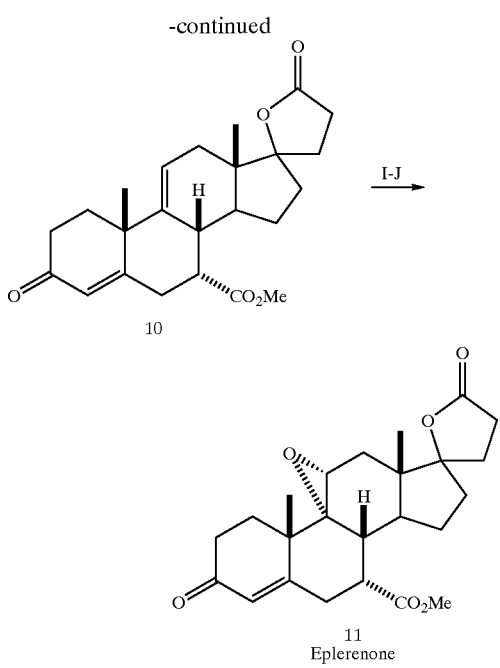

10

11
Eplerenone

Referring to Scheme I, intermediate 2 may be produce by adding hexamethyldisilazane (HMDS) (100 ml) to a stirred slurry of 50.0 g Triol 1 in 400 ml methylene chloride. Saccharin (0.57 g) is then added and the mixture is heated under reflux for 3 hours during which time the slurry will gradually dissolve to a clear, amber solution. Water (5 ml) is added to quench any excess HMDS. After 5 minutes at reflux the mixture is filtered through a $CH_2Cl_2$ wet layer of 32.6 g magnesol on a 350 ml coarse frit filter funnel. The filtrate should be clear and almost colorless. The filter cake is washed with 2×100 ml $CH_2Cl_2$. The combined filtrates are concentrated under reduced pressure and residual methylene chloride is removed by evaporation with 2×500 ml portions of tetrahydrofuran (THF), concentrating to dryness after each addition to give a white solid.

A suspension of potassium t-butoxide (42.0 g) in 500 ml THF is cooled to −9°±5° C. with an ice/methanol bath. Acetylene is bubbled into the mixture just under the surface with moderate stirring at for at least 1 hour. The silylated steroid intermediate from above in THF (400 ml) is added over 30 min while maintaining a reaction temperature of 0°±5° C. After the addition, the mixture is stirred for a further hour at 5°±5° C. Water (100 ml) is added slowly allowing the reaction mixture to warm up to 15°±5° C. 125 ml of 10% HCl is slowly added to reduce the pH to 2.5 to 3. The mixture is stirred at pH 2.5 to 3, adding small amounts of 5% HCl as needed to maintain a pH of 2.5 to 3, for 1 to 2 hours at 20°±5° C. When the hydrolysis is complete, half saturated $NaHCO_3$ solution is added to raise the pH to 5.5 to 6. The mixture is diluted with ethyl acetate (500 ml) and the phases separated. The aqueous phase is extracted with ethyl acetate and the combined ethyl acetate phases are washed with water, brine, dried over magnesium sulfate and concentrated to give the addition product 2.

The intermediate 2 may be acylated by dissolving tetraol 2 (50.00 g, 144 mmol) in pyridine (150 ml) and cooling the resulting mixture to <10° C. in an ice bath. Dimethylaminopyridine (DMAP) (1.7 g, 14 mmol) is added followed by slow addition of acetic anhydride (41.4 ml, 439 mmol) at a rate to maintain the solution temperature below 10° C. Following the addition, the reaction mixture is warmed to room temperature. The mixture is diluted with ethyl acetate (75 ml) and water (50 ml), stirred for 5 minutes and the layers separated. The organic layer is washed with 10% HCl (4×25 ml) followed by $H_2O$ (2×50 ml), dried over $MgSO_4$ and concentrated. The product is recrystallized from toluene (100 ml).

Hydroformylation of the acylated intermediate 3 may be produced by heating compound 3 (25.4 g, 54 mmol) with $PPh_3$ (2.13 g, 8.1 mmol) and $Rh_2(OAc)_4$ (716 mg, 1.62 mmol) in ethyl acetate (200 ml) to about 80° C. under a 1/1 mixture of hydrogen/carbon monoxide at a pressure of 170 psi for 12 hours. The mixture is concentrated under reduced pressure and the product 4 purified by column chromatography (70/30 EtOAc/Hex and 500 g silica).

Oxidation of the lactol compound 4 may be accomplished by mixing the lactol 4 (25 g, 50 mmol), methylene chloride (250 ml), water (38 ml), 2,2,6,6-tetramethylpiperidin-1-oxyl (TEMPO) (156 mg, 1 mmol), KBr (595 mg, 5 mmol), and $NaHCO_3$ (5.5 g, 65 mmol) and cooling the mixture to ≦10° C. in an ice bath. A solution of 1.1 M sodium hypochlorite (NaOCl) (50 ml, 55 mmol) is slowly added. The mixture is allowed to warm to room temperature and diluted with water (50 ml). The layers are separated and the organic layer washed with brine (2×50 ml). The organic layer is dried with $MgSO_4$, filtered and concentrated to afford 5 as an off white foam.

Heating a mixture of the triacetate 5 (2.0 g), $Pd(dppp)Br_2$ (126 mg), diisopropyl amine (0.78 mL), $Et_4NBr$ (260 mg), NaBr (1.09 g) in 20 ml of methanol under 1200 psi of CO at 65° C. for twelve hours, followed by cooling, concentrating, and chromatographing the residue on silica gel with 40–75% ethyl acetate/hexane gives the methyl ester 6.

A solution of the diacetylester 6 (5.01 g) in 0.15N potassium carbonate in methanol (50 ml) is stirred at room temperature and the reaction monitored by TLC. When the starting material 6 is no longer detected the mixture is diluted with water (200 ml) and extracted with ethyl acetate (3×200 ml). The combined extracts are washed with water (100 ml), brine (100 ml), dried over magnesium sulfate and concentrated at reduced pressure to dryness. The residue is chromatographed over silica gel with ethyl acetate/hexane gives the 3-hydroxy compound 7.

A mixture of alcohol 7 (6.0 g), $CH_2Cl_2$ (40 mL), water (9.0 mL), 2,2,6,6-tetramethylpiperidine-1-oxyl (TEMPO) (38 mg), KBr (142 mg) and sodium bicarbonate (4.0 g) is cooled to 5° C. To this mixture is slowly added 14.1 ml of 1.1 M NaOCl. After the addition the mixture is allowed to stir for an additional 1 h and acidified with dilute HCl. The product 8 is isolated with $CH_2Cl_2$.

A solution of the compound 8 (5.01 g) in 0.15N potassium carbonate in methanol (50 ml) is stirred at room temperature and the reaction monitored by TLC. When the starting material 8 is no longer detected the mixture is diluted with water (200 ml) and extracted with ethyl acetate (3×200 ml). The combined extracts are washed with water (100 ml), brine (100 ml), dried over magnesium sulfate and concentrated at reduced pressure to dryness. The residue is chromatographed over silica gel with ethyl acetate/hexane to give compound 9.

$PCl_5$ (1.08 g) is added to a solution of compound 9 in THF at −51° C. which results in a temperature rise to −48° C.

After 2 hrs the mixture is poured into aqueous NaHCO$_3$ and extracted with EtOAc and concentrated. The material was chromatographed on silica gel with EtOAc/hexane to afford the diene compound 10.

Eperlernone is produced by epoxidation of compound 10 by known methods described, for example, in U.S. Pat. Nos. 4,559,332, and 5,981,744, the contents of which are incorporated in their entirety by reference.

Referring to Chart A, androst-5-en-17-one compounds of formula (I) may be converted to different steroid intermediates via fungal reactions. For instance, contacting androst-5-en-17-one compounds of formula (I), where $Z_1$–$Z_2$ is either a single bond or a double bond, with *Diplodia gossypina* produces 7β-hydroxy androst-5-en-17-one compounds of formula (II). 11α-hydroxyandrost-5-en-17-one compounds of formula (III) are produced by contacting androst-5-en-17-one compounds of formula (I), where $Z_1$–$Z_2$ is a single bond, with *Aspergillus ochraceus*. Surprisingly, contacting 11α-hydroxyandrost-5-en-17-one compounds of formula (III) with *Diplodia gossypina* fails to produce the 7β,11α-dihydroxyandrost-5-en-17-one compounds of formula (IV), whereas contacting 7β-hydroxyandrost-5-en-17-one compounds of formula (II), where $Z_1$–$Z_2$ is a single bond, with *Aspergillus ochraceus* produces 7β,11α-dihydroxyandrost-5-en-17-one compounds of formula (IV). Unexpectedly, contacting androst-5-en-17-one compounds of formula (I), where $Z_1$–$Z_2$ is a single bond with *Absidia coerulea* directly produces 7β,11α-dihydroxyandrost-5-en-17-one compounds of formula (IV).

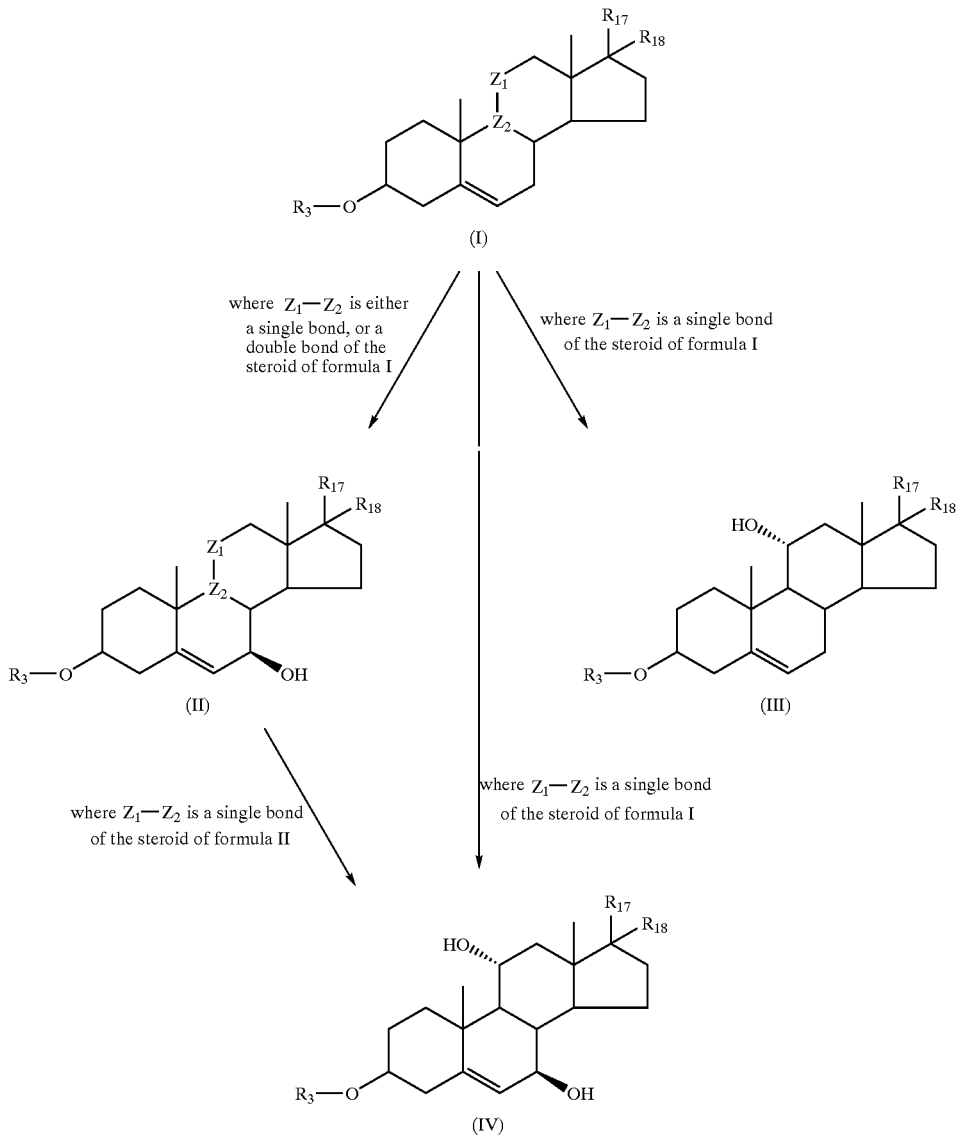

CHART A

The filamentous fungi reactants belong to the genera *Dipodia* (synonyms *Botryodiplodia*, *Lasiodiplodia*),

*Aspergillus*, and *Absidia coerulea*, and are generally prepared by a primary and a secondary vegetative seed stage. The secondary seed is utilized to inoculate the steroid bioconversion stage.

The processes disclosed herein may be used to produce steroid compounds of formula (I), (II), (III), and (IV), that are useful intermediates for the manufacture of pharmaceutically active steroids such as aldosterone receptor antagonists. In addition, 5-androsten-3β,7β-diol-17-one (formula II wherein $R_3$ is a hydrogen and $R_{17}$ and $R_{18}$ together are a ketone, and $Z_1-Z_2$ is a single bond) is an attractive intermediate for the synthesis of 5-androsten-3β-ol-7,17-dione, a commercially available steroid supplement that has been postulated to have beneficial effects on heart disease, immune function, aging, and general well-being.

Detailed Description of the 7β-Hydroxylation Step

Steroid compounds of formula (I), where $Z_1-Z_2$ is a single bond or a double bond, are microbiologically hydroxylated at the 7-position to produce steroid compounds of formula (II), where $Z_1-Z_2$ is a single bond or a double bond.

Any filamentous fungus of the genus *Diplodia, Botryodiplodia*, or *Lasiodiplodia* capable of 7β-hydroxylating steroids of formula (I) can be used in the invention process. Preferably, *Diplodia gossypina* ATCC 20571 (synonym *Botryodiplodia theobromae* IFO 6469) or *Botryodiplodia malorum* ATCC 24444 (synonym CBS 134.50) are used. More preferably, *Diplodia gossypina* ATCC 20571 (synonym *Botryodiplodia theobromae* IFO 6469) is used.

The fungal hydroxylase may be utilized in the form of an actively growing culture, a whole-cell concentrate, or a cell-free extract. Preferably the fungus is grown in submerged culture under aerobic conditions, using any art-recognized procedure, and the 7β-hydroxylation reaction performed in situ.

The desired fungus may be cultured under conditions set forth in EXAMPLEs 1 and 2 using the ingredients specified, or other suitable carbon and nitrogen sources as are known to those skilled in the art. Generally a primary and secondary vegetative seed procedure is used in preparation for the fungal 7β-hydroxylation. Alternatively, a primary vegetative seed can be used directly to inoculate bioconversion media.

Primary vegetative seed cultures may be incubated for a period of about 24 to about 96 hours (preferably about 48–72 hours) at a temperature between about 20° and about 37° (preferably about 28°), and a pH between about 3.0 and about 7.5. Secondary vegetative seed medium is inoculated with about 0.006% to about 0.1% (v/v) primary vegetative seed culture, but typically about 0.012% (v/v), and incubated for a period of about 36 to about 72 hours (preferably about 60 hours) at a temperature between about 20° and about 37° (preferably about 28°). The pH of the secondary seed medium can be between about 2.5 and about 7.0, but preferably between about 3.0 and about 5.0. The bioconversion medium, which can be the same or similar to the secondary vegetative seed medium, is inoculated with about 1% to about 10% (v/v) secondary vegetative seed culture (preferably about 3% to about 5%). After an initial incubation period of about 12 to about 72 hours (preferably about 16 to about 24 hours), steroid substrates of formula (I), preferably micronized, are added to the bioconversion culture. Micronized steroid substrates of formula (I) can be added as a dry powder or an aqueous slurry, either as a single addition, a series of additions, or a continual feed. It is preferred to use the micronized steroid substrates of formula (I) at a concentration greater than 1 g/L, more preferably greater than 2.5 g/L, even more preferably greater than 5 g/L. Bioconversion of steroid substrates of formula (I) to form 7β-hydroxylated products of formula (II), respectively, is allowed to proceed for between about 2 and about 6 days, but typically about 3 to about 4 days.

The rate and extent of 7β-hydroxylation can be greatly improved by: (i) culturing the selected fungus, and performing the bioconversion, in the presence of a detergent. The detergent may be selected from the group consisting of non-ionic detergents, but preferably the sub-groups consisting of ethoxylated alkylphenols and polyoxyethylenesorbitan esters. More preferably, polyoxyethylenesorbitan monooleate is used; (ii) culturing the selected fungus, and performing the bioconversion, in the presence of a natural oil. The natural oil may be selected from, but not restricted to, the group consisting of caster oil, corn oil, cottonseed oil, lard oil, linseed oil, olive oil, peanut oil, rapeseed oil, safflower seed oil, soybean oil, sunflower seed oil, and wheat germ oil. Preferably, soybean oil is used; (iii) using a combination of the methodologies identified in (i) and (ii).

Once the bioconversion of steroid substrates of formula (I) to 7β-hydroxylated products of formula (II) is complete, compounds of formula (II) can be isolated using any one of a number of art-recognized procedures. Preferably, filtered or centrifuged beer solids are extracted using an organic solvent, such as methanol, acetone, butyl acetate, or methylene chloride and the 7β-hydroxylated product of formula (II) is isolated by crystallization. The crystallization solvents include a solvent selected from, but not restricted to, the group consisting of water, methanol, acetone, butyl acetate, methylene chloride, or combinations thereof. The preferred extraction and crystallization solvent for the 7β-hydroxylated product of formula (II) is methylene chloride.

Detailed Description of the 11α-Hydroxylation Step

Steroid compounds of formula (I) or (II), where $Z_1-Z_2$ is a single bond are microbiologically hydroxylated at the 11-position to produce steroid compounds of formula (III) or (IV), respectively.

Any filamentous fungus of the genus *Aspergillus* capable of 11α-hydroxylating steroids of formula (I) or (II), where $Z_1-Z_2$ is a single bond can be used in the invention process. Preferably, *Aspergillus ochraceus* ATCC 18500 (synonym NRRL 405) is used.

The fungal hydroxylase may be utilized in the form of an actively growing culture, a whole-cell concentrate, or a cell-free extract. Preferably the fungus is grown in submerged culture under aerobic conditions, using any art-recognized procedure, and the 11α-hydroxylation reaction performed in situ.

The desired fungus may be cultured under conditions set forth in EXAMPLEs 3 and 4 using the ingredients specified, or other suitable carbon and nitrogen sources as are known to those skilled in the art. Generally a primary and secondary vegetative seed procedure is used in preparation for the fungal 11α-hydroxylation. Alternatively, a primary vegetative seed can be used directly to inoculate bioconversion media.

Primary vegetative seed cultures may be incubated for a period of about 24 to about 96 hours (preferably about 48–72 hours) at a temperature between about 20° and about 37° (preferably about 28°), and a pH between about 3.0 and about 7.5. Secondary vegetative seed medium is inoculated with about 0.006% to about 0.1% (v/v) primary vegetative seed culture, but typically about 0.012% (v/v), and incubated for a period of about 36 to about 72 hours (preferably about 60 hours) at a temperature between about 20° and about 37° (preferably about 28°). The pH of the secondary seed medium can be between about 2.5 and about 7.0, but preferably between about 3.0 and about 5.0. The bioconversion medium, which can be the same or similar to the secondary vegetative seed medium, is inoculated with about 1% to about 10% (v/v) secondary vegetative seed culture (preferably about 3% to about 5%). After an initial incubation period of about 12 to about 72 hours (preferably about 16 to about 24 hours), steroid substrates of formula (I) or (II), where $Z_1$–$Z_2$ is a single bond, are added to the bioconversion culture. Preferably the substrates are micronized. Micronized steroid substrates of formula (I) or (II), where $Z_1$–$Z_2$ is a single bond, can be added as a dry powder or an aqueous slurry, either as a single addition, a series of additions, or a continual feed. It is preferred to use the micronized steroid substrates of formula (I) or (II), where $Z_1$–$Z_2$ is a single bond, at a concentration greater than 1 g/L, more preferably greater than 2.5 g/L, even more preferably greater than 5 g/L. Bioconversion of steroid substrates of formula (I) or (II), where $Z_1$–$Z_2$ is a single bond, to form 11α-hydroxylated products of formula (III) or (IV), respectively, is allowed to proceed for between about 1 and about 6 days, but typically about 2 to about 3 days.

The rate and extent of 11α-hydroxylation can be greatly improved by: (i) culturing the selected fungus, and performing the bioconversion, in the presence of a detergent. The detergent may be selected from the group consisting of non-ionic detergents, but preferably the sub-groups consisting of ethoxylated alkylphenols and polyoxyethylenesorbitan esters. More preferably, octylphenoxypolyethoxyethanol or nonylphenoxypolyethoxyethanol is used; (ii) culturing the selected fungus, and performing the bioconversion, in the presence of natural oil. The natural oil may be selected from, but not restricted to, the group consisting of caster oil, corn oil, cottonseed oil, lard oil, linseed oil, olive oil, peanut oil, rapeseed oil, safflower seed oil, soybean oil, sunflower seed oil, and wheat germ oil. Preferably, soybean oil is used; (iii) using a combination of the methodologies identified in (i) and (ii).

Once the bioconversion of steroid substrates of formula (I) or (II), where $Z_1$–$Z_2$ is a single bond to 11α-hydroxylated products of formula (III) or (IV) is complete, compounds of formula (III) or (IV) can be isolated using any one of a number of art-recognized procedures. Preferably, filtered or centrifuged beer solids, or whole beers, are extracted using a water-miscible organic solvent, such as methanol or acetone at temperatures as low as about 15° C. or as high as about 55° C. The preferred extraction temperature is about 45–50° C. The crude 11α-hydroxylated product of formula (III) or (IV) is generated by evaporative crystallization, to remove the organic solvent, and cooling. The preferred extraction solvent mixture is 80–85% acetone/15–20% water. The spent aqueous liquor is discarded.

Crude crystalline 11α-hydroxylated product of formula (III) or (IV), is purified by carbon treatment and crystallization. It is preferred that the carbon treatment and subsequent crystallization be done using a water-miscible solvent selected from, but not restricted to, the group consisting of methanol or acetone. The preferred carbon-treatment/crystallization solvent is methanol. After removal of carbon by filtration, the crystallization is performed by evaporation of solvent and cooling.

Compounds of formula (I) where $Z_1$–$Z_2$ is a double bond may be produced by eliminating the 11α-hydroxyl from the product of formula (III) using known chemical methods.

Detailed Description of the 7β,11α-Dihydroxylation Step

Steroid compounds of formula (I), where $Z_1$–$Z_2$ is a single bond are microbiologically hydroxylated at the 7- and 11-position, in a single step, to produce steroid compounds of formula (IV).

Any filamentous fungus of the genus *Absidia* capable of 7β,11α-dihydroxylating steroids of formula (I), where $Z_1$–$Z_2$ is a single bond can be used in the invention process. Preferably, *Absidia coerulea* ATCC 6647 (synonym *Absidia orchidis*) is used.

The fungal hydroxylase(s) may be utilized in the form of an actively growing culture, a whole-cell concentrate, or a cell-free extract. Preferably the fungus is grown in submerged culture under aerobic conditions, using any art-recognized procedure, and the 7β- and 11α-hydroxylation reactions performed in situ.

The desired fungus may be cultured under conditions set forth in EXAMPLE 5 using the ingredients specified, or other suitable carbon and nitrogen sources as are known to those skilled in the art. Generally a primary and secondary vegetative seed procedure is used in preparation for the fungal 7β,11α-dihydroxylation. Alternatively, a primary vegetative seed can be used directly to inoculate bioconversion media.

Primary vegetative seed cultures may be incubated for a period of about 24 to about 96 hours (preferably about 48–72 hours) at a temperature between about 20° and about 37° (preferably about 28°), and a pH between about 3.0 and about 7.5. Secondary vegetative seed medium, which can be the same or similar to the primary vegetative seed medium, is inoculated with about 0.006% to about 0.1% (v/v) primary vegetative seed culture, but typically about 0.012% (v/v), and incubated for a period of about 36 to about 96 hours (preferably about 70 to 80 hours) at a temperature between about 20° and about 37° (preferably about 28°). The pH of the secondary seed medium can be between about 2.5 and about 7.5, but preferably between about 3.0 and about 7.0. The bioconversion medium, which can be the same or similar to the secondary vegetative seed medium, is inoculated with about 1% to about 10% (v/v) secondary vegetative seed culture (preferably about 3% to about 5%). After an initial incubation period of about 12 to about 72 hours (preferably about 15 to about 24 hours), steroid substrates of formula (I), where $Z_1$–$Z_2$ is a single bond, are added to the bioconversion culture. Preferably the substrates are micronized. Micronized steroid substrates of formula (I), where $Z_1$–$Z_2$ is a single bond, can be added as a dry powder or an aqueous slurry, either as a single addition, a series of additions, or a continual feed. It is preferred to use the micronized steroid substrates of formula (I), where $Z_1$–$Z_2$ is a single bond, at a concentration greater than 1 g/L, more preferably greater than 2.5 g/L, even more preferably greater than 5 g/L. Bioconversion of steroid substrates of formula (I), where $Z_1$–$Z_2$ is a single bond, to form 11α-hydroxylated products of formula (IV), is allowed to proceed for between about 2 and about 9 days, but typically about 5 to about 7 days. Once the bioconversion of steroid substrates of formula (I), where $Z_1$–$Z_2$ is a single bond, to 7β,11α-dihydroxylated products of formula (IV) is complete, compounds of formula (IV) can be isolated using any one of a number of art-recognized procedures. Preferably, filtered or centrifuged beer solids, or whole beers, are extracted using a water-miscible organic solvent, such as methanol or acetone at temperatures as low as about 15° C. or as high as about 55° C. The preferred extraction temperature is about 45–50° C. The crude 7β,11α-dihydroxylated product of formula IV is generated by evaporative crystallization, to remove the organic solvent, and cooling. The preferred extraction solvent mixture is 80% acetone/20% water. The spent aqueous liquor is discarded.

Crude crystalline 7β,11α-dihydroxylated product of formula (IV) is purified by a methylene chloride trituration to remove unwanted impurities, followed by carbon treatment and crystallization. It is preferred that the carbon treatment and subsequent crystallization be done using a water-miscible solvent selected from, but not restricted to, the group consisting of methanol or acetone or mixtures. The preferred carbon-treatment/crystallization solvent is methanol. After removal of carbon by filtration, product crystallization is achieved by evaporation of the solvent and cooling.

EXAMPLES

Without further elaboration, it is believed that one skilled in the art can, using the preceding descriptions, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

3β-hydroxyandrost-5-en-17-one, also referred to as 5-androsten-3β-ol-17-one, is available from Jiangsu Wujin Pharmaceuticals located in China.

Example 1

Bioconversion of 5-androsten-3β-ol-17-one (I, Where $R_3$=Hydrogen, $R_{17,18}$=Ketone, and $Z_1$–$Z_2$ is a Single Bond to 5-androsten-3β,7β-diol-17-one (II, Where $R_3$=Hydrogen, $R_{17,18}$=Ketone, and $Z_1$–$Z_2$ is a Single Bond)

The bioconversion of 5-androsten-3β-ol-17-one to 5-androsten-3β,7β-diol-17-one is performed using a submerged culture of *Diplodia gossypina* ATCC 20571 (synonym *Botryodiplodia theobromae* IFO 6469) at a 10-L fermentation scale.

(A) Primary-Seed Stage

Frozen vegetative cells of *Diplodia gossypina* ATCC 20571 are thawed, transferred to potato-dextrose-agar plates (PDA), and incubated at 28° for 72 hours. Single mycelial-plugs (6–7 mm diam.) are used to inoculate siliconized 500-mL stippled shakeflasks containing 100 mL primary-seed medium. Primary-seed medium consists of (per liter of RO water): dextrin, 50 g; soyflour, 35 g; cerelose, 5 g; cobalt chloride hexahydrate, 2 mg; silicone defoamer (SAG 471), 0.5 mL; pre-sterilization pH 7.0–7.2, adjusted with sodium hydroxide (2N). *Diplodia gossypina* ATCC 20571 is incubated for 48 hours at 28°, using a controlled-environment incubator-shaker set at 280 r.p.m. (1" orbital stroke).

(B) Secondary-Seed Stage

Ten-liter secondary-seed fermentations are inoculated using 1.2 mL vegetative primary-seed culture (0.012% [v/v] inoculation rate). Secondary-seed medium contains (per liter of RO water): cerelose, 60 g; soyflour, 25 g; soybean oil, 30 mL; magnesium sulfate heptahydrate, 1 g; potassium dihydrogen phosphate, 0.74 g; polyoxyethylenesorbitan monooleate, 2 mL; silicone defoamer (SAG 471), 0.5 mL; pre-sterilization pH 3.95–4.00, adjusted with concentrated sulfuric acid. The fermentors, containing secondary-seed medium, are sterilized for 20 minutes at 121° using both jacket and injection steam. The agitation rate during sterilization is 200 r.p.m. Post-sterilization, the medium pH is adjusted to 4.0 using sterile sulfuric acid (5%). *Diplodia gossypina* ATCC 20571 is incubated at 28° using the following initial parameters: agitation, 100 r.p.m.; back pressure=5 psig; airflow=2.5 SLM (0.25 VVM); low DO set-point, 30%; pH control, none. When the DO first drops to 30%, the airflow is increased to 5 SLM (0.5 VVM). When the culture reaches low DO again, 30% DO is maintained using agitation control. Secondary-seed cultures are harvested at approximately 60 hours post-inoculation, when the OUR is between about 10 and about 15 mM/L/h.

(C) Steroid Bioconversion

Ten-liter steroid-bioconversion fermentations are inoculated using 500 mL vegetative secondary-seed culture (5% [v/v] inoculation rate). Steroid-bioconversion medium is the same as secondary-seed medium. Sterilization conditions and pH adjustment are as described for secondary-seed medium. *Diplodia gossypina* ATCC 20571 is incubated at 28° using essentially the same initial parameters as those used for secondary-seed cultivation, with the exception that the low DO set-point is increased from 30% to 50%. When the DO first drops to 50%, the air flow is increased from 2.5 SLM (0.25 VVM) to 5 SLM (0.5 VVM). When the culture reaches low DO again, 50% DO is maintained using agitation control. Starting at 24 hours post-inoculation, micronized 5-androsten-3β-ol-17-one, slurried in a minimal volume of 0.2% polyoxyethylenesorbitan monooleate, is added to the fermentation in one-hour intervals until 400 g total is added. At about 3 days post-inoculation, an additional 100 g cerelose is added to the 10-L fermentation.

Bioconversion cultures are assayed on a daily basis for 5-androsten-3β,7βp-diol-17-one using TLC. One milliliter of whole beer is extracted with 10 mL methanol. Cells are separated from the aqueous-methanol mixture by centrifugation (3,000×g for 10 minutes), and several microliters applied to a TLC plate. The TLC plate is developed in cyclohexane:ethyl acetate:methanol (90:60:15) and the product visualized by spraying the TLC with 50% sulfuric acid, followed by charring in an oven. Product is compared with authentic standard, which turns blue on spraying with 50% sulfuric acid. Bioconversion of 5-androsten-3β-ol-17-one to 5-androsten-3β,7βp-diol-17-one is complete approximately 4 days post-inoculation.

(D) Isolation Procedure

The whole beer at harvest is centrifuged and the rich solids are recovered by centrifugation. The rich solids are extracted with 10 liters of methylene chloride and the rich extract is recovered by centrifugation. The extract is polished and concentrated to about 1-liter by distillation and the crystal slurry is cooled to –10° C. The crystals are recovered by filtration, washed with cold methylene chloride to remove color, and dried to give 227 grams of purified crystalline 5-androsten-3β,7β-diol-17-one.

Example 2

Bioconversion of 5,9(11)-androstadien-3β-ol-17-one (I, Where $R_3$=Hydrogen, $R_{17,18}$=Ketone, and $Z_1$–$Z_2$ is a Double Bond to 5,9(11)-androstadien-3β,7β-diol-17-one (II, Where $R_3$=Hydrogen, $R_{17,18}$=Ketone, and $Z_1$–$Z_2$ is a Double Bond The bioconversion of 5,9(11)-androstadien-3β-ol-17-one to 5,9(11)-androstadien-3β,7β-diol-17-one is performed using a submerged culture of *Diplodia gossypina* ATCC 20571 (synonym *Botryodiplodia theobromae* IFO 6469) at a 10-L fermentation scale.

(A) Primary-Seed Stage

Primary-seed cultures are prepared as described in EXAMPLE 1.

(B) Secondary-Seed Stage

Ten-liter secondary-seed cultures are prepared as described in EXAMPLE 1.

(C) Steroid Bioconversion

Ten-liter steroid-bioconversion cultures are prepared as described in EXAMPLE 1. At about 24 hours post-inoculation, 120 g micronized 5,9(11)-androstadien-3β-ol-17-one, slurried in a minimal volume of 0.2% polyoxyethylenesorbitan monooleate, is added to the 10-L fermentation.

Bioconversion cultures are assayed on a daily basis for 5,9(11)-androstadien-3β,7β-diol-17-one using the procedure described in EXAMPLE 1. Bioconversion of 5,9(11)-androstadien-3β-ol-17-one to 5,9(11)-androstadien-3β,7β-diol-17-one is complete approximately 3 days post-inoculation.

(D) Isolation Procedure

The rich solids from the whole beer are recovered by centrifugation. The liquid beer phase is extracted using 15 liters of methylene chloride. After settling, the upper spent beer layer is decanted and discarded. The remaining rich methylene chloride is then used to extract the rich solids. The resulting rich methylene chloride extract is drained from the spent solids, polished, concentrated by distillation to about 0.5 liters, and cooled to −10 C. The crystals obtained are recovered by filtration, washed with n-butyl acetate to remove color, and dried to give 52.2 grams of purified crystalline 5,9(11)-androstadien-3β,7β-diol-17-one.

Example 3

Bioconversion of 5-androsten-3β-ol-17-one (I, Where $R_3$=Hydrogen, $R_{17,18}$=Ketone, and $Z_1$–$Z_2$ is a Single Bond to 5-androsten-3β,11α-diol-17-one (II, Where $R_3$=Hydrogen, $R_{17,18}$=Ketone, and $Z_1$–$Z_2$ is a Single Bond)

The bioconversion of 5-androsten-3β-ol-17-one to 5-androsten-3β,11α-diol-17-one is performed using a submerged culture of *Aspergillus ochraceus* ATCC 18500 (synonym NRRL 405) at a 10-L fermentation scale.

(A) Primary-Seed Stage

Primary-seed cultures of *Aspergillus ochraceus* ATCC 18500 are prepared as described for *Diplodia gossypina* ATCC 20571 in EXAMPLE 1.

(B) Secondary-Seed Stage

Ten-liter secondary-seed fermentations are inoculated using 1.2 mL vegetative primary-seed culture (0.012% [v/v] inoculation rate). Secondary-seed medium contains (per liter of RO water): cerelose, 40 g; soyflour, 25 g; soybean oil, 30 mL; magnesium sulfate heptahydrate, 1 g; potassium dihydrogen phosphate, 0.74 g; nonylphenoxypolyethoxyethanol, 0.25 mL; silicone defoamer (SAG 471), 0.5 mL; pre-sterilization pH 3.95–4.00, adjusted with concentrated sulfuric acid. The fermentors, containing secondary-seed medium, are sterilized for 20 minutes at 121° using both jacket and injection steam. The agitation rate during sterilization is 200 r.p.m. Post-sterilization, the medium pH is adjusted to 4.0 using sterile sulfuric acid (5%). *Aspergillus ochraceus* ATCC 18500 is incubated at 28° using the following initial parameters: agitation, 100 r.p.m.; back pressure=5 psig; airflow=2.5 SLM (0.25 VVM); low DO set-point, 50%; pH control, none. When the DO first drops to 50%, the airflow is increased to 5 SLM (0.5 VVM). When the culture reaches low DO again, 50% DO is maintained using agitation control. Secondary-seed cultures are harvested between 50 to 54 hours post-inoculation, when the OUR is between about 20 and about 26 mM/L/h.

(C) Steroid Bioconversion

Ten-liter steroid-bioconversion fermentations are inoculated using 500 mL vegetative secondary-seed culture (5% [v/v] inoculation rate). Steroid-bioconversion medium is essentially the same as secondary-seed medium, with the exception that the nonylphenoxypolyethoxyethanol is increased from 0.25 mL/L to 2 mL/L, and pre-sterilization pH is adjusted to 2.95–3.00 with concentrated sulfuric acid. Sterilization conditions are as described for secondary-seed medium. Post-sterilization, the medium pH is adjusted to 3.0 using sterile sulfuric acid (5%). *Aspergillus ochraceus* ATCC 18500 is incubated at 28° using essentially the same initial parameters as those used for secondary-seed cultivation, with the exception that agitation is initially set at 200 r.p.m. At about 18 hours post-inoculation, 200 g micronized 5-androsten-3β-ol-17-one, slurried in a minimal volume of 0.2% nonylphenoxypolyethoxyethanol, is added to the 10-L fermentation.

Bioconversion cultures are assayed on a daily basis for 5-androsten-3β,11α-diol-17-one using TLC. One milliliter of whole beer is extracted with 19 mL methanol. Cells are separated from the aqueous-methanol mixture by centrifugation (3,000×g for 10 minutes), and several microliters applied to a TLC plate. The TLC plate is developed in cyclohexane:ethyl acetate:methanol (90:60:15) and the product visualized by spraying the TLC with 50% sulfuric acid, followed by charring in an oven. Bioconversion of 5-androsten-3β-ol-17-one to 5-androsten-3β,11α-diol-17-one is complete approximately 3 days post-inoculation.

(D) Isolation Procedure

The whole beer solids are recovered by centrifugation. The liquid is discarded. The rich solids are extracted with 10 liters of 85% acetone 15% water at 45° C. to 50° C. and the rich extract is recovered by centrifugation. The extract is concentrated by distillation to remove acetone to generate an aqueous slurry of crude crystals. The crude crystals are recovered by filtration and the mother liquor is discarded. The water-wet crude crystals are dissolved in 700 milliliters of methanol by heating to 55° C. and then decolorized with 5 grams of Darco G-60 carbon. After filtration to remove carbon, the filtrate is concentrated to crystallize the product. The methanol is removed further by adding 300 mL of n-butyl acetate and concentrating to a thick crystal slurry. The crystals are filtered, washed with n-butyl acetate, and dried to give 174 grams of purified crystalline 5-androsten-3β,11α-diol-17-one.

Example 4

Bioconversion of 5-androsten-3β,7β-diol-17-one (II, Where $R_3$=Hydrogen, $R_{17,18}$=Ketone, and $Z_1$–$Z_2$ is a Single Bond to 5-androsten-3β,7β, 11α-triol-17-one (IV, Where $R_3$=Hydrogen, $R_{17,18}$=Ketone)

The bioconversion of 5-androsten-3β,7β-diol-17-one to 5-androsten-3β,7β,11α-triol-17-one is performed using a submerged culture of *Aspergillus ochraceus* ATCC 18500 (synonym NRRL 405) at a 10-L fermentation scale.

(A) Primary-Seed Stage

Primary-seed cultures of *Aspergillus ochraceus* ATCC 18500 are prepared as described in EXAMPLE 3.

(B) Secondary-Seed Stage

Ten-liter secondary-seed cultures of *Aspergillus ochraceus* ATCC 18500 are prepared as described in EXAMPLE 3.

(C) Steroid Bioconversion

Ten-liter steroid-bioconversion cultures of *Aspergillus ochraceus* ATCC 18500 are prepared as described in EXAMPLE 3.

At about 18 hours post-inoculation, 200 g micronized 5-androsten-3β,7β-diol-17-one, slurried in a minimal volume of 0.2% nonylphenoxypolyethoxyethanol, is added to the 10-L fermentation.

Bioconversion cultures are assayed on a daily basis for 5-androsten-3β,7β,11α-triol-17-one using TLC, as described in EXAMPLE 1. Bioconversion of 5-androsten-3β,7β-diol-17-one to 5-androsten-3β,7β,11α-triol-17-one is complete approximately 4 days post-inoculation.

(D) Isolation Procedure

The whole beer solids are recovered by centrifugation. The liquid is discarded. The rich solids are extracted with 10 liters of 80% acetone 20% water at 45° C. to 50° C. and the warm extract is clarified by filtration. The rich filtrate is concentrated by distillation to remove acetone generating an aqueous slurry of crude crystals. The crude crystals are recovered by filtration and the mother liquor is discarded. The water-wet crystals are triturated in 600 milliliters of methylene chloride to remove impurities, dissolved in 700 milliliters of methanol (by heating to 55° C.), and then decolorized with 5 grams of Darco G-60 carbon. After filtration to remove carbon, the filtrate is concentrated to crystallize the product. The methanol is removed further by adding 300 mL of n-butyl acetate and concentrating to a thick crystal slurry. The crystals are filtered, washed with n-butyl acetate, and dried to give 158 grams of purified crystalline 5-androsten-3β,7β,11α-triol-17-one.

Example 5

Bioconversion of 5-androsten-3β-ol-17-one (I, Where $R_3$=Hydrogen, $R_{17,18}$=Ketone, and $Z_1$–$Z_2$ is a Single Bond to 5-androsten-3β,7β,11α-triol-17-one (IV, Where $R_3$=Hydrogen, $R_{17,18}$=Ketone)

The bioconversion of 5-androsten-3β-ol-17-one to 5-androsten-3β,7β,11α-triol-17-one is performed using a submerged culture of *Absidia coerulea* ATCC 6647 (synonym *Absidia orchidis*) at a 10-L fermentation scale.

(A) Primary-Seed Stage

Primary-seed cultures of *Absidia coerulea* ATCC 6647 are prepared as described for *Diplodia gossypina* ATCC 20571 in EXAMPLE 1.

(B) Secondary-Seed Stage

Ten-liter secondary-seed fermentations are inoculated using 1.2 mL vegetative primary-seed culture (0.012% [v/v] inoculation rate). Secondary-seed medium contains (per liter of RO water): dextrin, 50 g; soyflour, 35 g; cerelose, 5 g; cobalt chloride hexahydrate, 2 mg; silicone defoamer (SAG 471), 0.5 mL; pre-sterilization pH 4.95–5.00, adjusted with concentrated sulfuric acid. The fermentors, containing secondary-seed medium, are sterilized for 20 minutes at 121° using both jacket and injection steam. The agitation rate during sterilization is 200 r.p.m. Post-sterilization, the medium pH is adjusted to 5.0 using sterile sulfuric acid (5%). *Absidia coerulea* ATCC 6647 is incubated at 28° using the following initial parameters: agitation, 100 r.p.m.; back pressure=5 psig; airflow=2.5 SLM (0.25 VVM); low DO set-point, 50%; pH control, none. When the DO first drops to 30%, the airflow is increased to 5 SLM (0.5 VWM). When the culture reaches low DO again, 30% DO is maintained using agitation control. Secondary-seed cultures are harvested about 76 hours post-inoculation, when the OUR is between about 4 and about 7 mM/L/h.

(C) Steroid Bioconversion

Ten-liter steroid-bioconversion fermentations are inoculated using 500 mL vegetative secondary-seed culture (5% [v/v] inoculation rate). Steroid-bioconversion medium contains (per liter of RO water): dextrin, 50 g; soyflour, 35 g; cerelose, 20 g; silicone defoamer (SAG 471), 0.5 mL; pre-sterilization pH 2.95–3.00, adjusted with concentrated sulfuric acid. Sterilization conditions are as described for secondary-seed medium. Post-sterilization, the medium pH is adjusted to 3.0 using sterile sulfuric acid (5%). *Absidia coerulea* ATCC 6647 is incubated at 28° using the same initial parameters as those used for secondary-seed cultivation. At about 17 hours post-inoculation, 200 g micronized 5-androsten-3β-ol-17-one, slurried in a minimal volume of 0.2% octylphenoxypolyethoxyethanol, is added to the 10-L fermentation.

Bioconversion cultures are assayed on a daily basis for 5-androsten-3β,7β,11α-triol-17-one using TLC, as described in EXAMPLE 1. Bioconversion of 5-androsten- 3β-ol-17-one to 5-androsten-3β,7β,11α-triol-17-one is complete approximately 6–7 days post-inoculation.

(D) Isolation Procedure

The whole beer solids are recovered by centrifugation. The liquid is discarded. The rich solids are extracted using 10 liters of 85% acetone 15% water at 45° C. to 50° C. and the warm extract is clarified by filtration. The rich filtrate is concentrated by distillation to remove acetone generating an aqueous slurry of crude crystals. The crystal slurry is filtered and the mother liquor is discarded. The water-wet crystals are triturated in 600 milliliters of methylene chloride to remove impurities, dissolved in 700 milliliters of methanol (by heating to 55° C.), and then decolorized with 5 grams of Darco G-60 carbon. After filtration to remove carbon, the filtrate is concentrated to crystallize the product. The methanol is removed further by adding 300 mL of n-butyl acetate and concentrating to a thick crystal slurry. The crystals are filtered, washed with n-butyl acetate, and dried to give 75.5 grams of crude crystalline 5-androsten-3β,7β,11α-triol-17-one.

The crude crystals are triturated in 600 milliliters of methylene chloride to remove additional impurities, dissolved in 700 milliliters of methanol (by heating to 55° C.), and then decolorized with 5 grams of Darco G-60 carbon. After filtration to remove carbon, the filtrate is concentrated to crystallize the product. The methanol is removed further by adding 300 mL of n-butyl acetate and concentrating to a thick crystal slurry. The crystals are filtered, washed with n-butyl acetate, and dried to give 42.1 grams of purified crystalline 5-androsten-3β,7β,11α-triol-17-one.

Example 6

Preparation of 5,9(11)-androstadien-3β-ol-17-one from 5-androsten-3β,11αo-diol-17-one

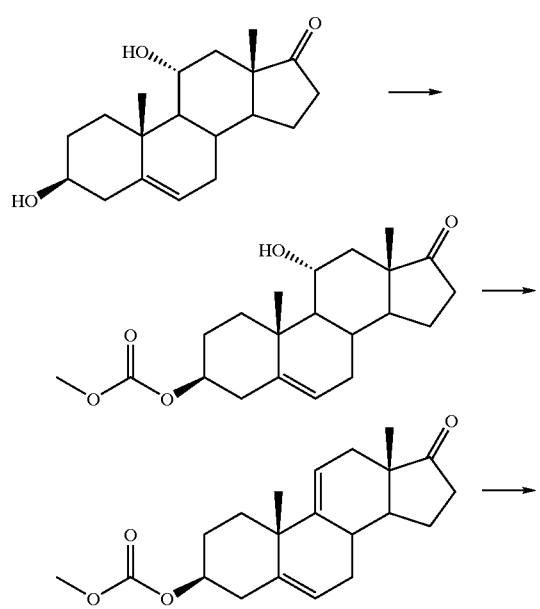

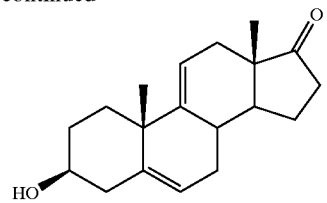

Step 1

To a slurry of 5-androsten-3β,11α-diol-17-one (30.4g, 100 mmol) in $CH_2Cl_2$ (300 mL) was added TMEDA (18.1 mL, 120 mmol). The slurry was cooled to −10° C. and methyl chloroformate (7.72 mL, 100 mmol) added. The reaction was allowed to warm to room temperature. The reaction was not complete by TLC so more methyl chloroformate (772 μL, 10 mmol) was added. When the reaction was determine to be complete by TLC, EtOAc (300 mL) and $H_2O$ (100 mL) were added and the resulting layers separated. The organic phase was washed with 50 mL $H_2O$, dried over $MgSO_4$ and concentrated to an oil which solidified on standing. The crude product was recrystallized from hot EtOAc/$CH_2Cl_2$ and heptane. The slurry was further cooled to 0–5° C. and the product collected by filtration (22 g, 60.8% chemical). The carbonate was further purified by column chromatography over silica gel eluting with a gradient of 5%–20% acetone/$CH_2Cl_2$ to obtain pure mono carbonate (20.57, 56.8%).

Step 2

The carbonate of step 1 (38.0 g, 0.105 mol) was dissolved in 570 mL of THF and cooled to −35° C. Solid $PCl_5$ (37.1 g, 0.178 mol) was slowly added keeping the temperature below −30° C. When TLC showed complete reaction the mixture was poured into cold $NaHCO_3$ solution and the product extracted with ethyl acetate. The organic layers were dried over $MgSO_4$ and concentrated to afford an oil.

Step 3

This oil of step 2 was dissolved in methanol (500 ml) and treated with 36.1 g of $K_2CO_3$ and the mixture stirred at room temperature 15hr. The residual carbonate was removed by filtration. The solution was partially concentrated and water added to precipitate the desired dienic alcohol, which was dried in an oven at 45° C. Yield 29.52 g.

The invention claimed is:

1. A 7β, 11α-dihydroxy steroid of the formula (IV)

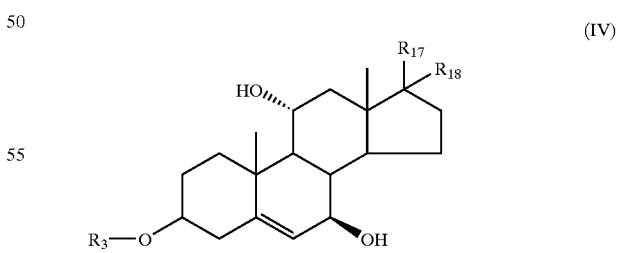

where $R_3$ is
—CO—$R_4$
$R_4$ is H $C_1$–$C_5$ alkyl; and
$R_{17}$ and $R_{18}$ together form =O.

2. The 7β, 11α-dihydroxy steroid (IV) according to claim 1, wherein $R_3$ is —C(O)—$CH_3$.

* * * * *